US006755808B2

(12) United States Patent
Balogh et al.

(10) Patent No.: US 6,755,808 B2
(45) Date of Patent: Jun. 29, 2004

(54) ABSORBENT GARMENT HAVING A BODY COMFORMING ABSORBENT COMPOSITE

(75) Inventors: Bridget A. Balogh, Menasha, WI (US);
David F. Bishop, Appleton, WI (US);
Danielle K. Minnich, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 44 days.

(21) Appl. No.: 10/053,251

(22) Filed: Nov. 2, 2001

(65) Prior Publication Data

US 2003/0088230 A1 May 8, 2003

(51) Int. Cl.[7] ............................ A61F 13/15; A61F 13/20
(52) U.S. Cl. ............................ 604/385.28; 604/385.01; 604/394
(58) Field of Search ................ 604/385.01, 385.03, 604/385.22, 385.24–385.3, 392–399

(56) References Cited

U.S. PATENT DOCUMENTS

| 4,704,115 A | 11/1987 | Buell |
| 4,704,116 A | 11/1987 | Enloe |
| 4,834,740 A | 5/1989 | Suzuki et al. |
| RE33,106 E | 11/1989 | Beckestrom |
| 4,880,420 A | 11/1989 | Pomparelli |
| 4,900,317 A | 2/1990 | Buell |
| 4,998,929 A | 3/1991 | Bjorksund et al. |
| 5,085,654 A | 2/1992 | Buell |
| 5,114,420 A | 5/1992 | Igaue et al. |
| 5,135,522 A | 8/1992 | Fahrenkrug et al. |
| 5,236,428 A | 8/1993 | Zajaczkowski |
| 5,263,949 A | 11/1993 | Karami et al. |
| 5,275,590 A | 1/1994 | Huffman et al. |
| 5,292,316 A | 3/1994 | Suzuki |
| 5,360,422 A | 11/1994 | Brownlee et al. |
| 5,387,210 A | 2/1995 | Murakami |
| 5,490,847 A | 2/1996 | Correa et al. |
| 5,540,672 A | 7/1996 | Roessler et al. |
| 5,599,417 A | 2/1997 | Glaug et al. |
| 5,601,544 A | 2/1997 | Glaug et al. |

(List continued on next page.)

FOREIGN PATENT DOCUMENTS

| DE | 198 13 334 | | 9/1999 |
| EP | 0 907 510 | | 3/2002 |
| GB | 2 253 131 A | | 9/1992 |
| JP | 1298202 A | * | 12/1989 |
| JP | 03176053 | | 7/1991 |
| JP | 3-205053 | | 9/1991 |
| JP | 4144558 A | * | 5/1992 |
| WO | 96/14815 | | 5/1996 |
| WO | 97/31603 | | 9/1997 |

OTHER PUBLICATIONS

International Search Report, International application No. PCT/US 02/26702, mailed Feb. 26, 2002.

Primary Examiner—Karin Reichle
(74) Attorney, Agent, or Firm—Brinks Hofer Gilson & Lione

(57) ABSTRACT

An absorbent garment includes a body panel and an absorbent composite having a longitudinally extending length and a laterally extending width and including a backsheet, a topsheet and a retention portion disposed between the backsheet and the topsheet. The absorbent composite is connected to the body panel and includes a side margin that is not attached to the body panel and that extends laterally outboard and terminates in a free edge. In one preferred embodiment, the free edge does not extend along the entirety of the length of the absorbent composite. Rather, the entire width of an end of the absorbent composite is secured to the body panel. Preferably, the width of the side margin along the portion of the absorbent composite overlapping the body panel is relatively constant.

11 Claims, 15 Drawing Sheets

U.S. PATENT DOCUMENTS

| | | |
|---|---|---|
| 5,624,424 A | 4/1997 | Saisaka et al. |
| 5,662,636 A | 9/1997 | Benjamin et al. |
| 5,704,928 A | 1/1998 | Morita et al. |
| 5,776,121 A | 7/1998 | Roe et al. |
| 5,782,819 A | 7/1998 | Tanzer et al. |
| 5,858,012 A | 1/1999 | Yamaki et al. |
| 6,056,733 A | 5/2000 | Kielpikowski |
| 6,083,212 A | 7/2000 | Kumasaka |
| 6,120,488 A | 9/2000 | VanRijswijck et al. |
| 6,129,720 A | 10/2000 | Blenke et al. |
| 6,132,410 A | 10/2000 | Van Gompel et al. |
| 6,152,908 A | 11/2000 | Widlund et al. |
| 6,174,302 B1 | 1/2001 | Kumasaka |
| 6,217,563 B1 | 4/2001 | Van Gompel et al. |
| 6,238,380 B1 | 5/2001 | Sasaki |
| 6,264,641 B1 | 7/2001 | Van Gompel et al. |
| 6,312,420 B1 | 11/2001 | Sasaki et al. |
| 6,336,922 B1 | 1/2002 | Van Gompel et al. |
| 6,361,527 B1 | 3/2002 | Van Gompel et al. |
| 6,364,862 B1 | 4/2002 | Yamamoto et al. |
| 6,375,646 B1 | 4/2002 | Widlund et al. |
| 6,478,786 B1 | 11/2002 | Glaug et al. |

(List continued on next page.)

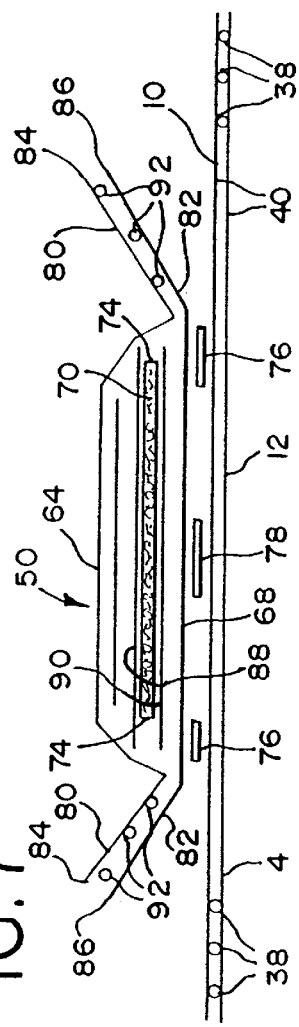

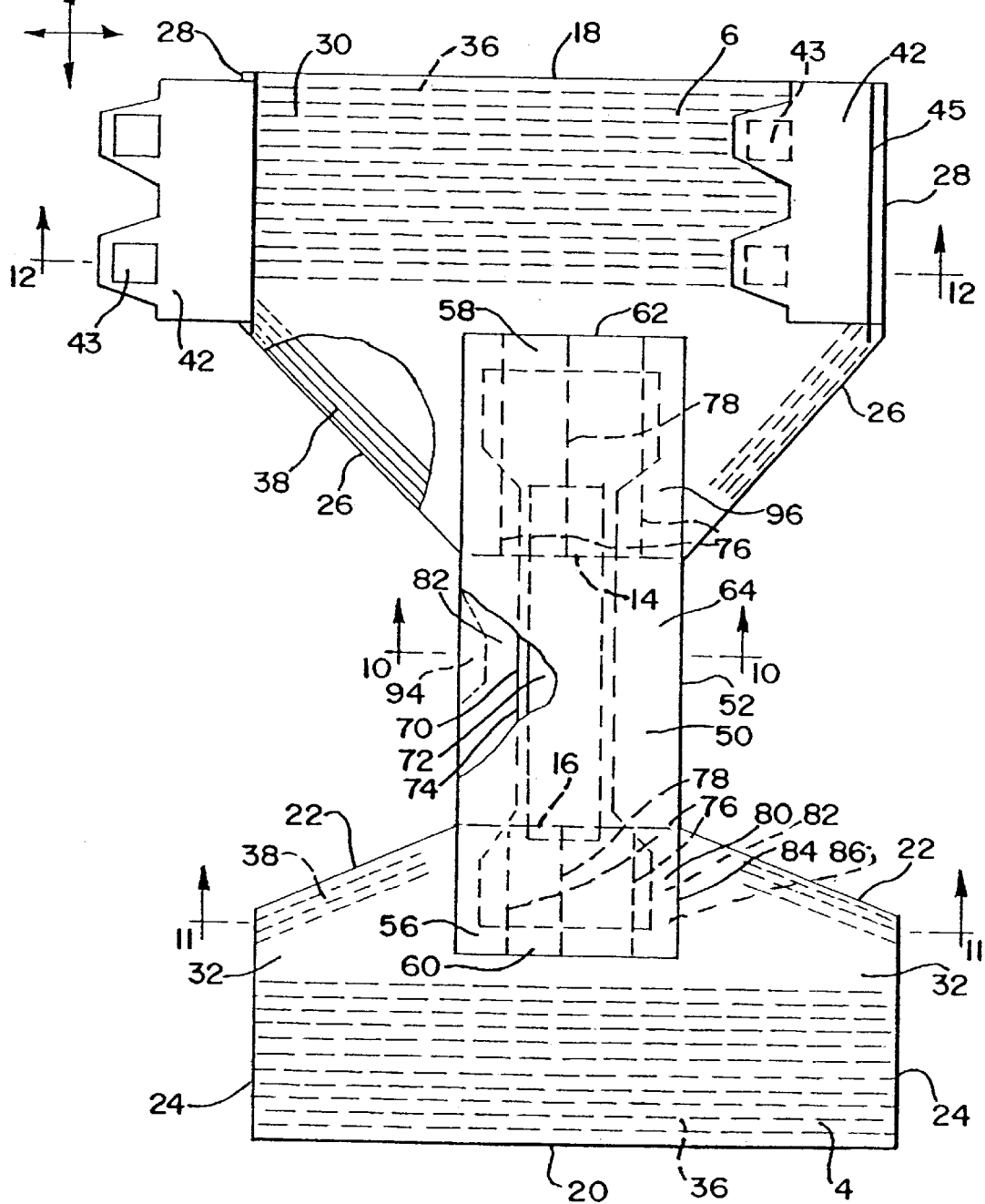

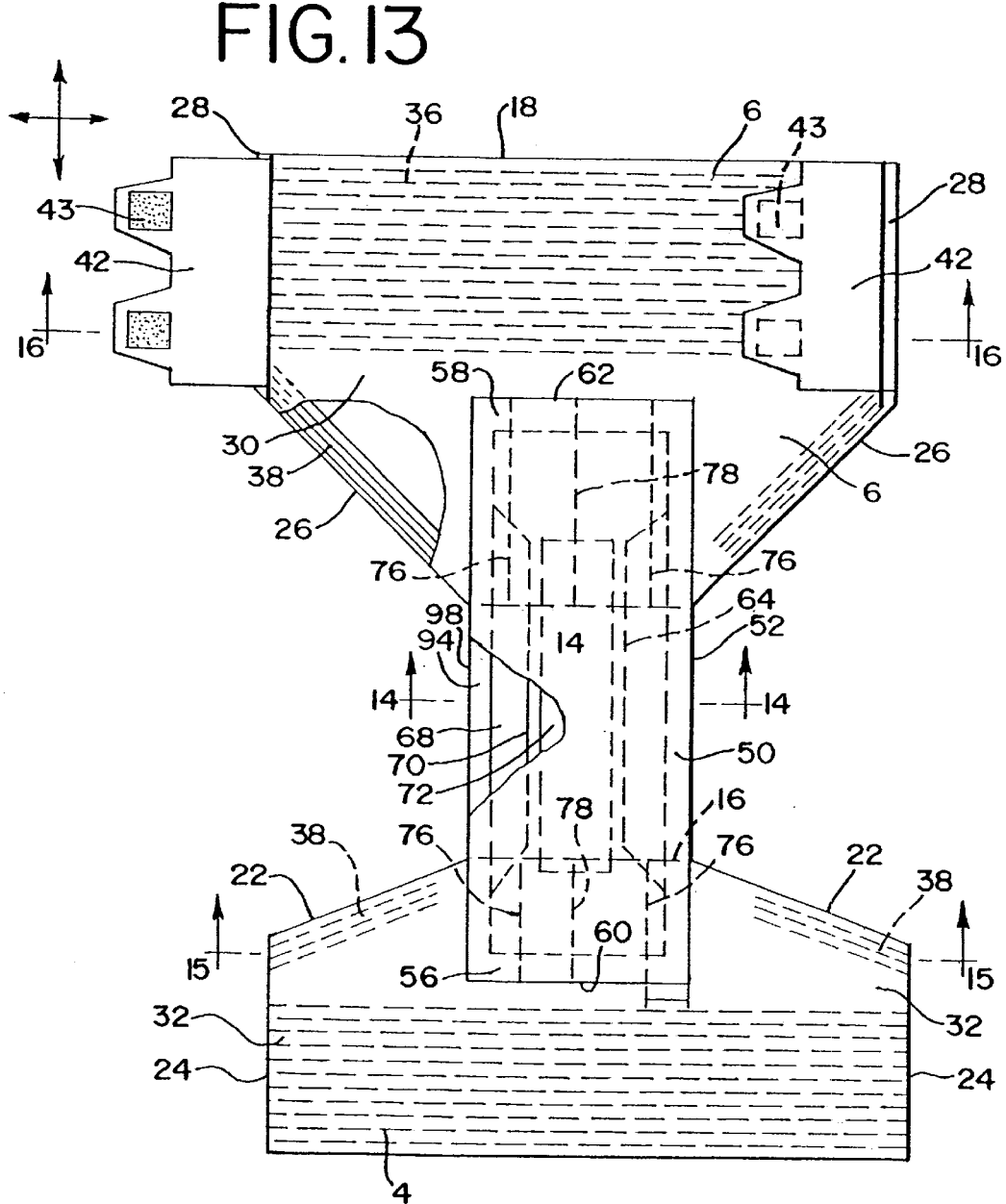

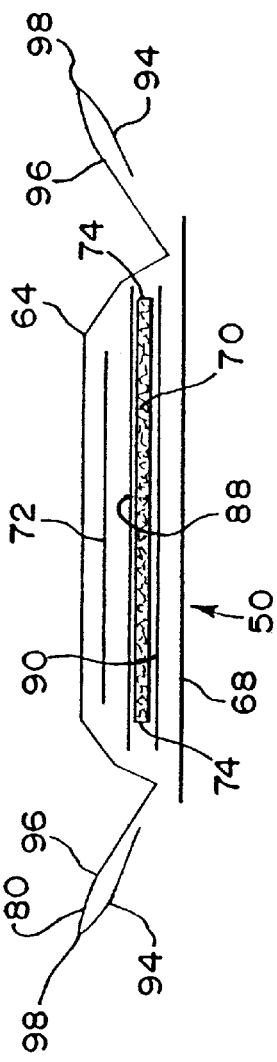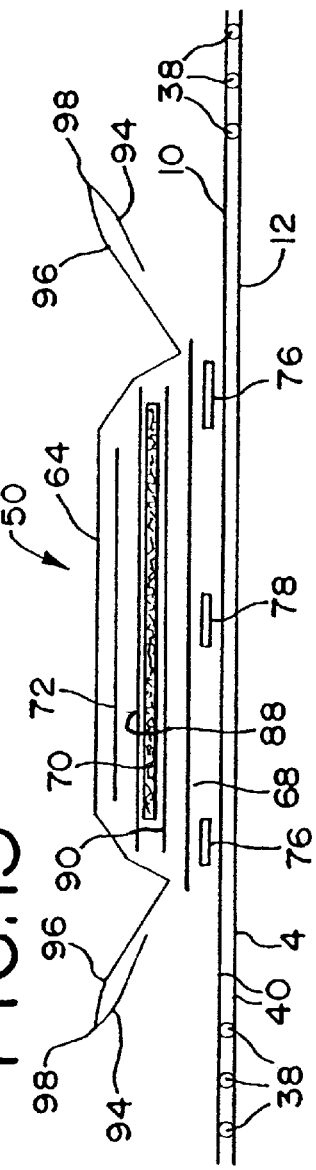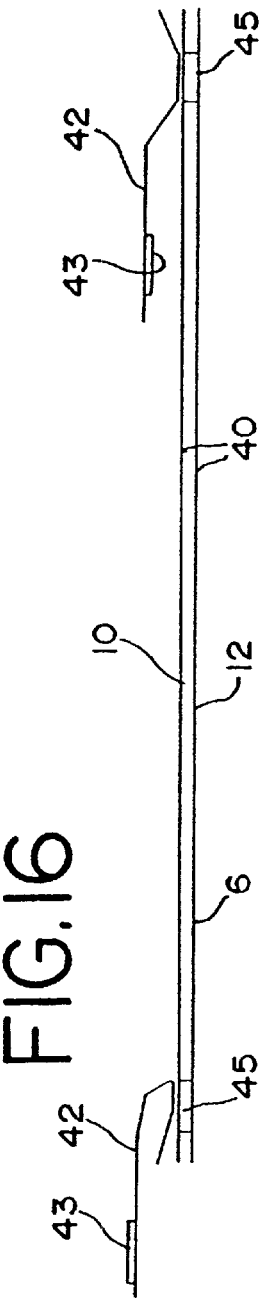

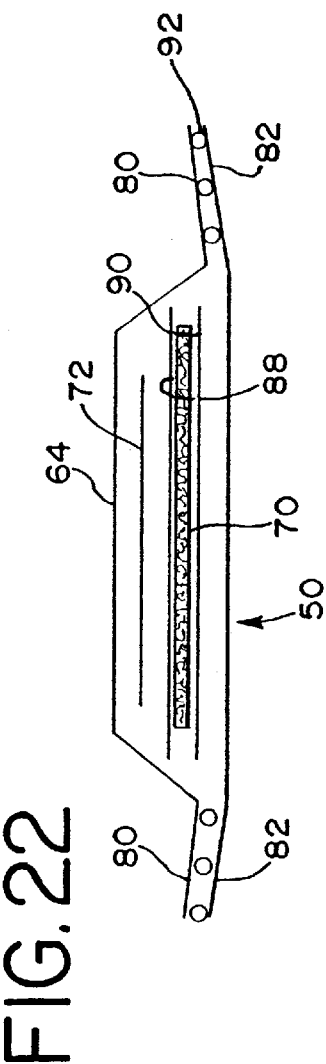
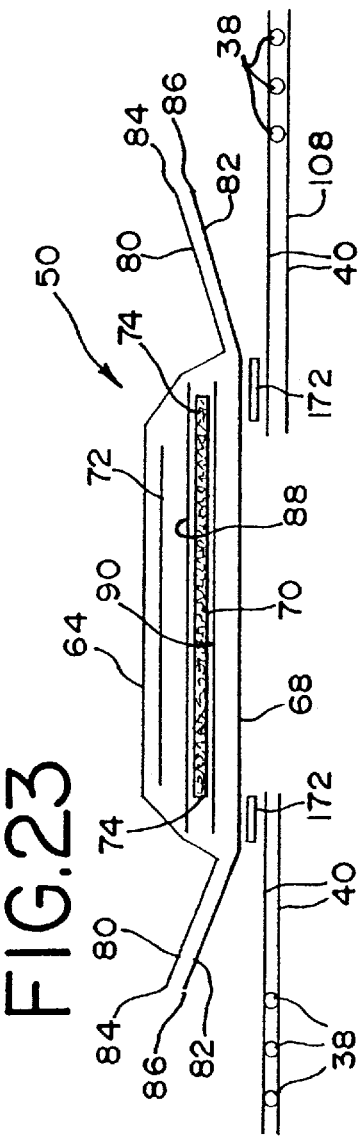
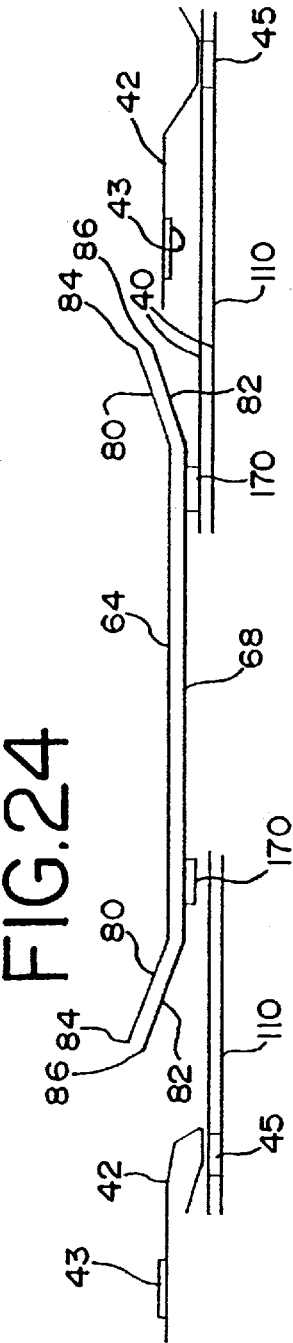
FIG.22
FIG.23
FIG.24

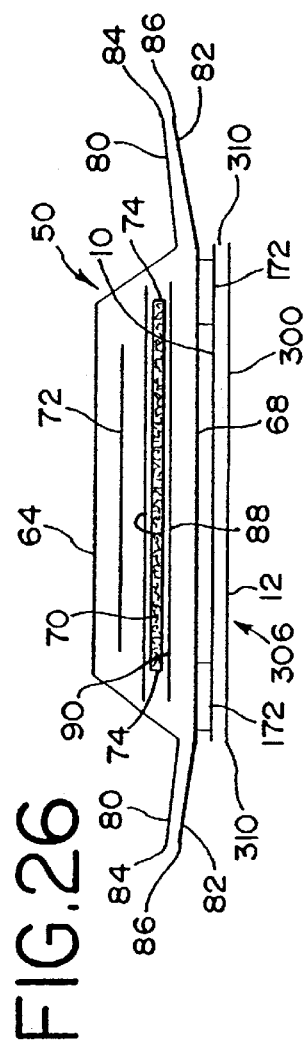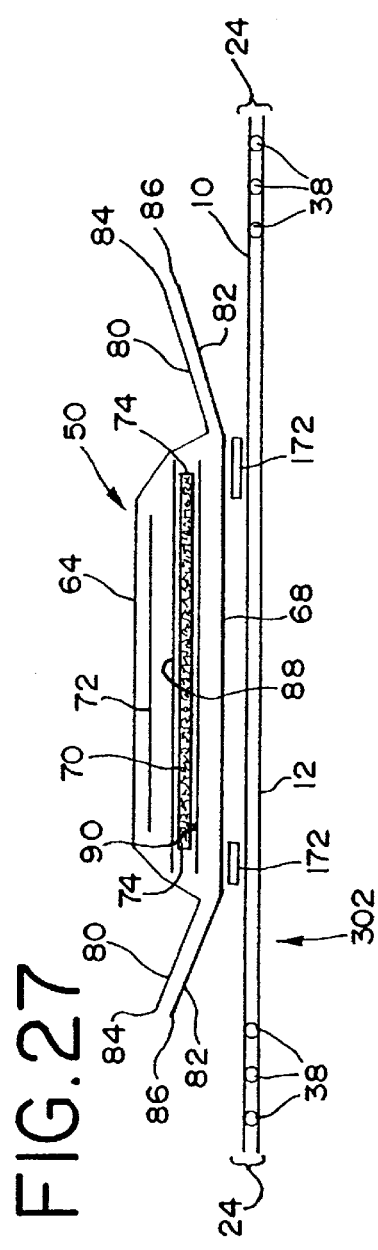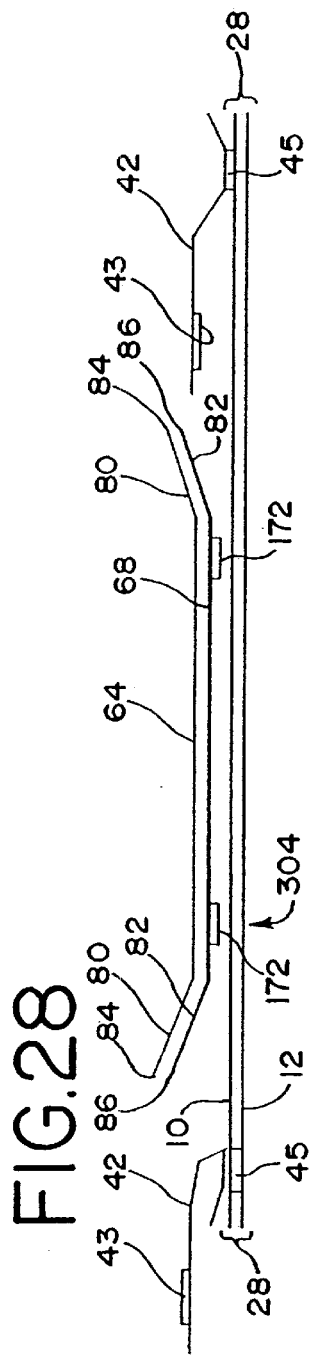

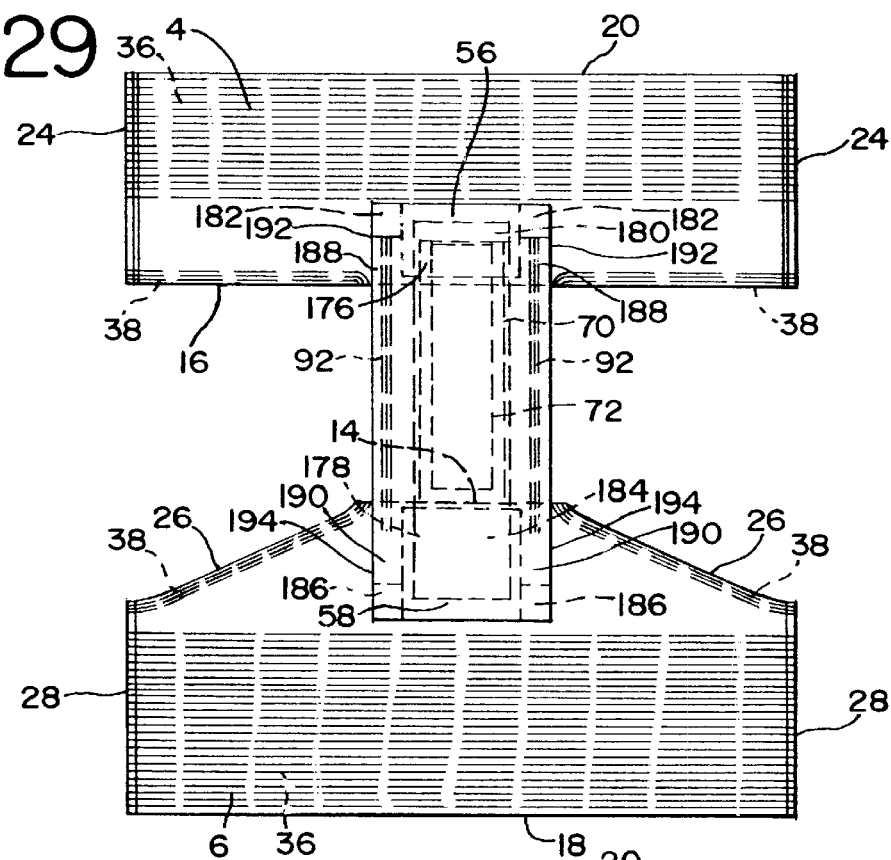
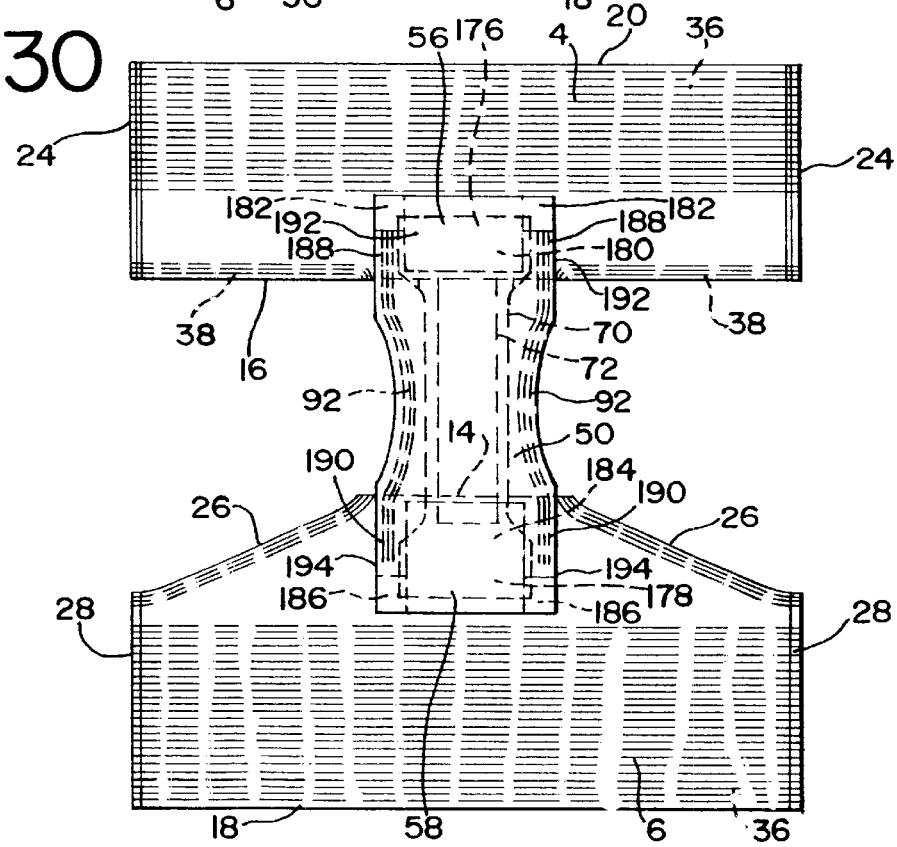

ABSORBENT GARMENT HAVING A BODY COMFORMING ABSORBENT COMPOSITE

BACKGROUND

The present invention relates generally to an absorbent garment, and in particular, to an absorbent garment having a body conforming absorbent composite.

Absorbent garments, and in particular disposable absorbent garments, often include an absorbent composite and one or more body panels connected to the absorbent composite. Typically, the absorbent composites are secured to the body panels along the peripheral side edges of the absorbent composite. As such, the absorbent composite can reduce or otherwise affect the extensibility of the body panel, especially when it is desired to have a wider absorbent composite. In addition, the absorbent composite typically is not able to conform to the body of the user independently of the body panels, and can therefore distort the panels when fitted to a user.

In other embodiments, the absorbent garment may include a top sheet and backsheet, one or both of which can form in part longitudinally extending flaps. Typically, such flaps are directed inboard to form a trough and may have one or more ends thereof secured to the garment to prevent the inversion thereof. As such, the flaps do not contribute to the overall width of the absorbent composite.

SUMMARY

Briefly stated, in one aspect, the invention is directed to an absorbent garment comprising a body panel having a bodyside surface and an absorbent composite having a longitudinally extending length and a laterally extending width and comprising a backsheet, a topsheet and a retention portion disposed between the backsheet and the topsheet. The absorbent composite is connected to the bodyside surface of the body panel and comprises a side margin that is not attached to the body panel and that extends laterally outboard and terminates in a free edge. The absorbent composite also is preferably connected to the body panel along an entirety of the laterally extending width at a laterally extending location at an end of the absorbent composite. The side margin and free edge extends longitudinally from the laterally extending location. Preferably, in one embodiment, the side margin has a relatively constant width.

In one preferred embodiment, the absorbent composite is connected to the body panel with a T-shaped attachment pattern. Also in a preferred embodiment, the absorbent composite includes laterally opposed side margins.

In one preferred embodiment, the side margin is formed from the top sheet. In another preferred embodiment, the side margin is formed from the topsheet and the backsheet. In one preferred embodiment, a first portion of the topsheet is folded over a second portion of the topsheet to form a folded edge that defines the free edge of the side margin. In yet another preferred embodiment, the backsheet is disposed between the first and second portions of the topsheet. Portions of the side margins can include an elastic element.

In one preferred embodiment, the body panel comprises a first and second longitudinally spaced body panels. In yet another preferred embodiment, each of the first and second body panels includes a pair of laterally spaced side body panels.

In another aspect of the invention, a method of protecting a user from bodily exudates comprises applying the absorbent garment to the body of the user.

The present invention provides significant advantages over other absorbent garments and methods for the use and manufacture thereof. For example, the unattached side margins can fold inward and follow the bodylines of the user without distorting the body panels. Moreover, the unattached side margins do not restrict the fit of the leg regions of the panels during use. In addition, the absorbent capacity of the garment can be easily changed simply by increasing the width of the absorbent composite, while at the same time maintaining the width of the portion of the absorbent composite that is connected to the body panels. As such, the width of the side margins can be increased without affecting the overall fit of the garment. In addition, the elastic elements can stand up or help seal or gasket the side margins against the user's body. At the same time, the configuration of the outwardly extending side margins ensures that the side margins, especially when they incorporate a moisture barrier, does not fold over the absorbent area defined by the retention portion, especially when the side margin includes elastic elements.

The present invention, together with further objects and advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

FIG. 6 is a schematic illustration of a cross-sectional view of the absorbent garment taken along line 6-6 in FIG. 5.

FIG. 7 is a schematic illustration of a cross-sectional view of the absorbent garment taken along line 7-7 in FIG. 5.

FIG. 8 is a schematic illustration of a cross-sectional view of the absorbent garment taken along line 8-8 in FIG. 5.

FIG. 9 is a plan view of a third embodiment of an absorbent garment taken from the bodyside thereof with a portion of the garment partially cut away.

FIG. 13 is a plan view of a fourth embodiment of an absorbent garment taken from the bodyside thereof with a portion of the garment partially cut away.

FIG. 14 is a schematic illustration of a cross-sectional view of the absorbent garment taken along line 14-14 in FIG. 13.

FIG. 15 is a schematic illustration of a cross-sectional view of the absorbent garment taken along line 15-15 in FIG. 13.

FIG. 16 is a schematic illustration of a cross-sectional view of the absorbent garment taken along line 16-16 in FIG. 13.

FIG. 22 is a schematic illustration of a cross-sectional view of the absorbent garment taken along line 22-22 in FIG. 21.

FIG. 23 is a schematic illustration of a cross-sectional view of the absorbent garment taken along line 23-23 in FIG. 21.

FIG. 24 is a schematic illustration of a cross-sectional view of the absorbent garment taken along line 24-24 in FIG. 21.

FIG. 26 is a schematic illustration of a cross-sectional view of the absorbent garment taken along line 26-26 in FIG. 25.

FIG. 27 is a schematic illustration of a cross-sectional view of the absorbent garment taken along line 27-27 in FIG. 25.

FIG. 28 is a schematic illustration of a cross-sectional view of the absorbent garment taken along line 28-28 in FIG. 25.

FIG. 29 is a plan view of a eighth embodiment of an absorbent garment taken from the bodyside thereof.

FIG. 30 is a plan view of an eighth ninth embodiment of an absorbent garment taken from the bodyside thereof.

DETAILED DESCRIPTION OF THE PRESENTLY PREFERRED EMBODIMENTS

Figure 1:
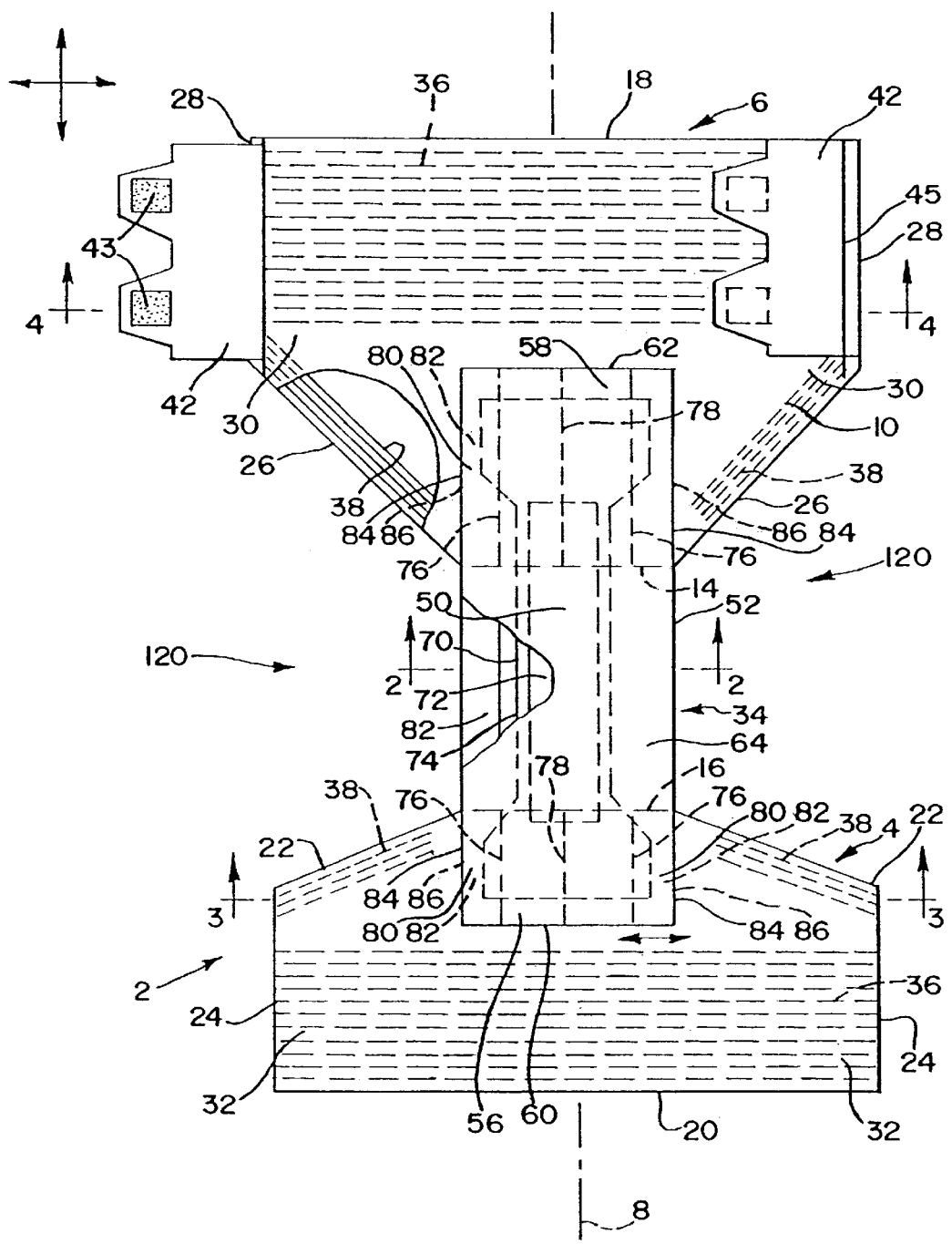
FIG. 1 is a plan view of a first embodiment of an absorbent garment taken from the bodyside thereof with a portion of the garment partially cut away.
Figure 2:
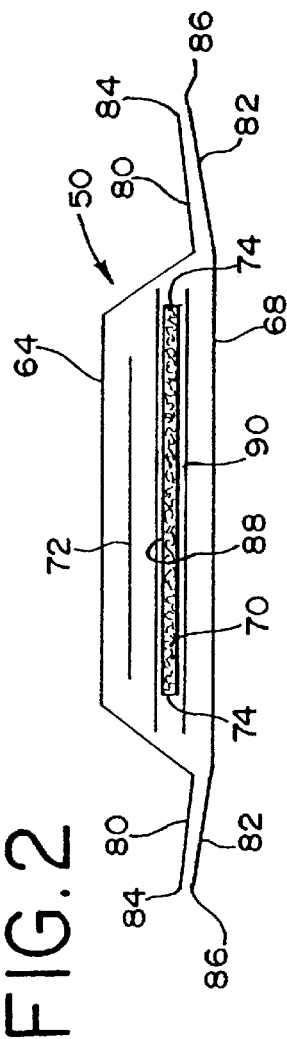
FIG. 2 is a schematic illustration of a cross-sectional view of the absorbent garment taken along line 2-2 in FIG. 1.
Figure 3:
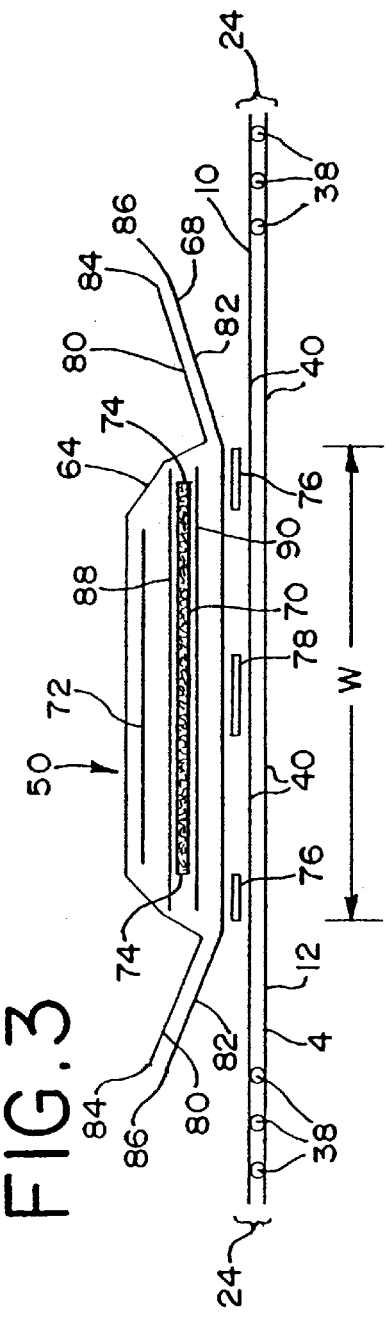
FIG. 3 is a schematic illustration of a cross-sectional view of the absorbent garment taken along line 3-3 in FIG. 1.
Figure 4:
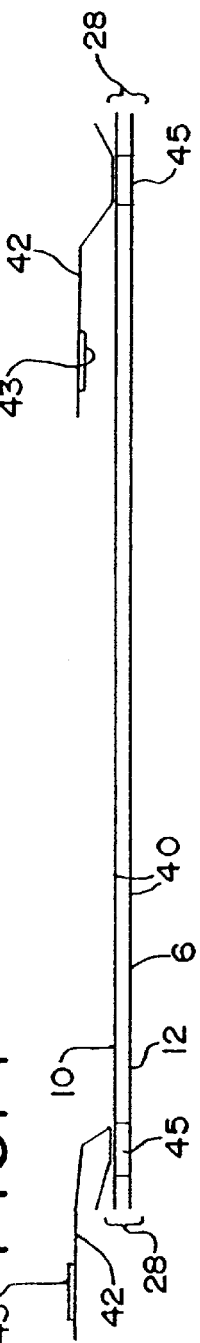
FIG. 4 is a schematic illustration of a cross-sectional view of the absorbent garment taken along line 4-4 in FIG. 1.
Figure 5:
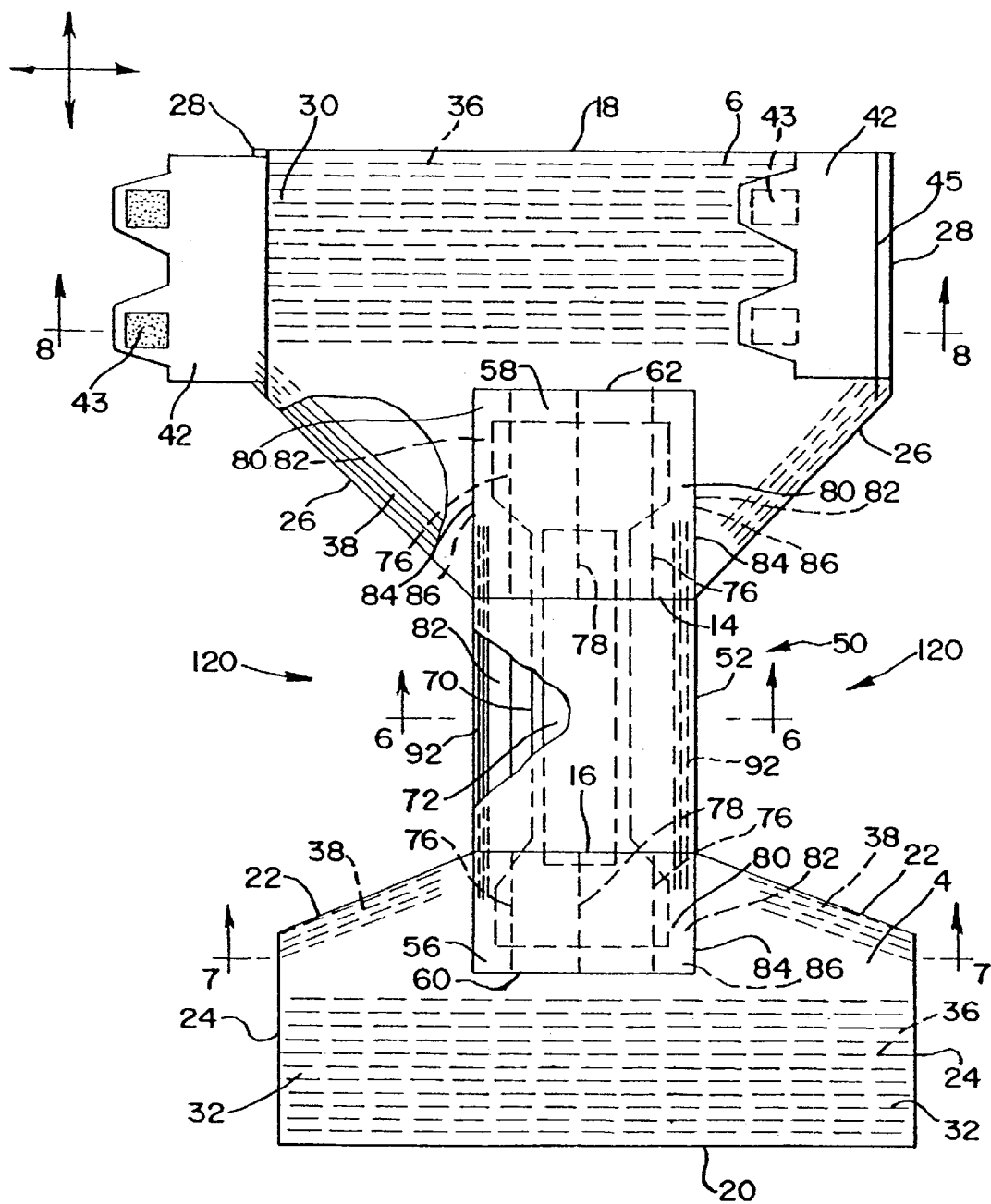
FIG. 5 is a plan view of a second embodiment of an absorbent garment taken from the bodyside thereof with a portion of the garment partially cut away.
Figure 10:
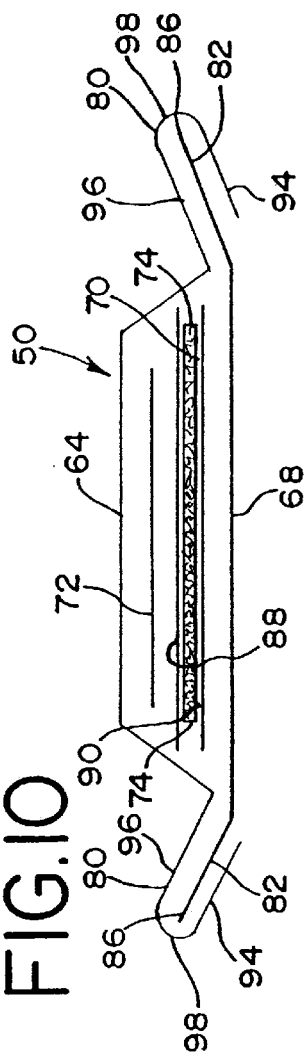
FIG. 10 is a schematic illustration of a cross-sectional view of the absorbent garment taken along line 10-10 in FIG. 9.
Figure 11:
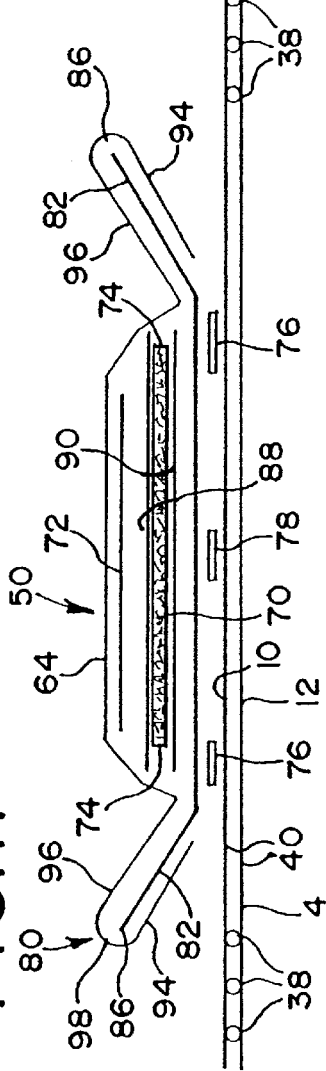
FIG. 11 is a schematic illustration of a cross-sectional view of the absorbent garment taken along line 11-11 in FIG. 9.
Figure 12:
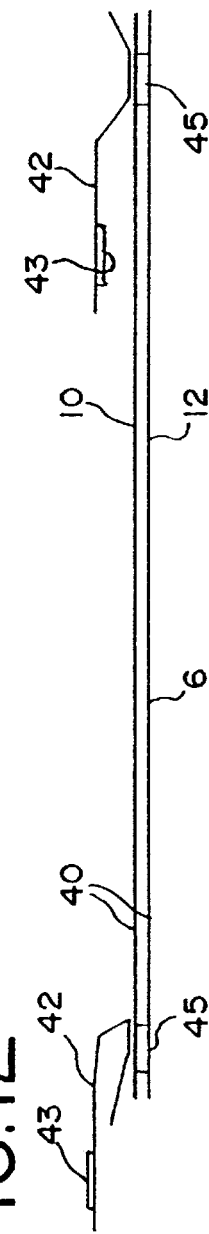
FIG. 12 is a schematic illustration of a cross-sectional view of the absorbent garment taken along line 12-12 in FIG. 9.
Figure 17:
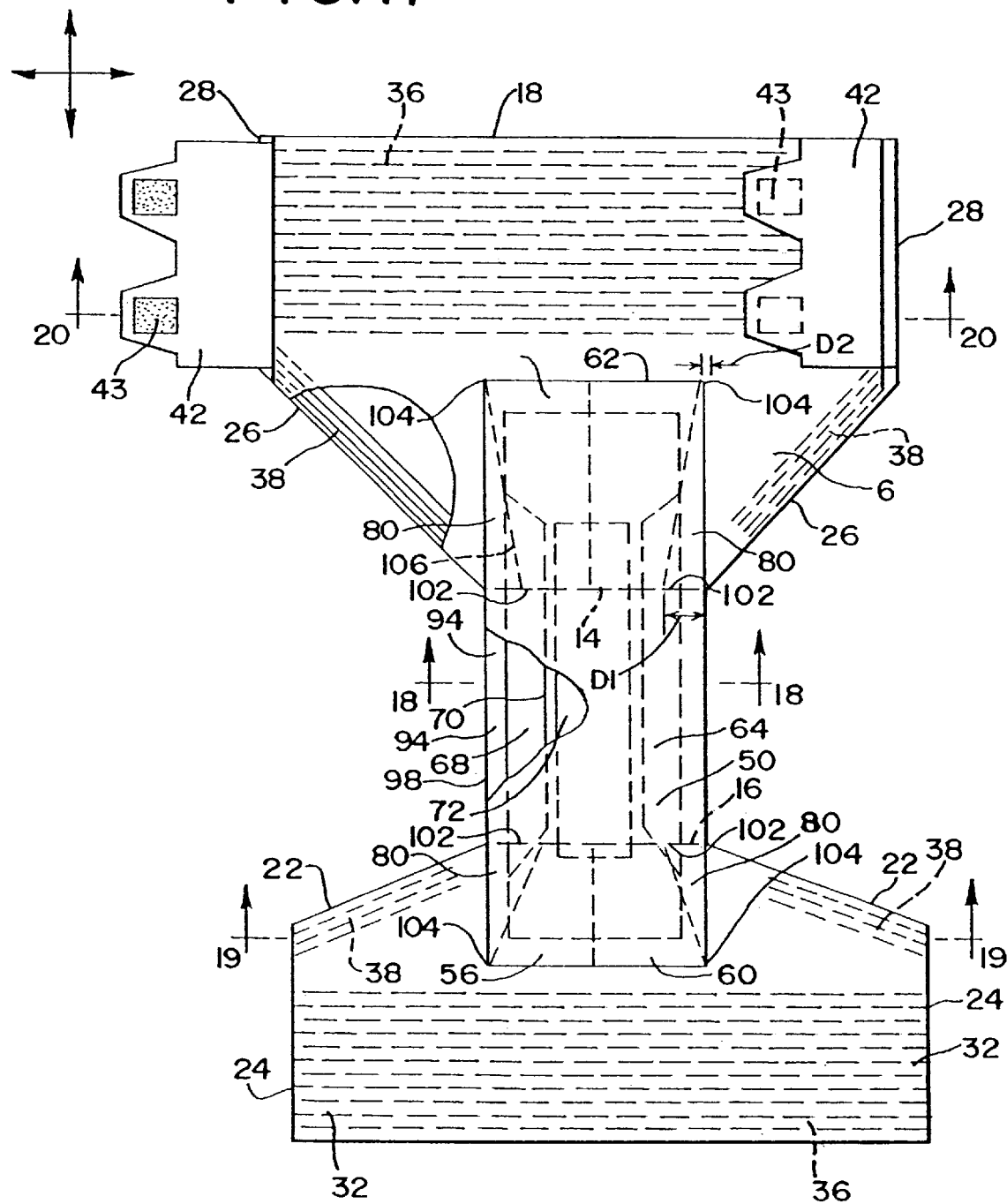
FIG. 17 is a plan view of a fifth embodiment of an absorbent garment taken from the bodyside thereof with a portion of the garment partially cut away.
Figure 18:
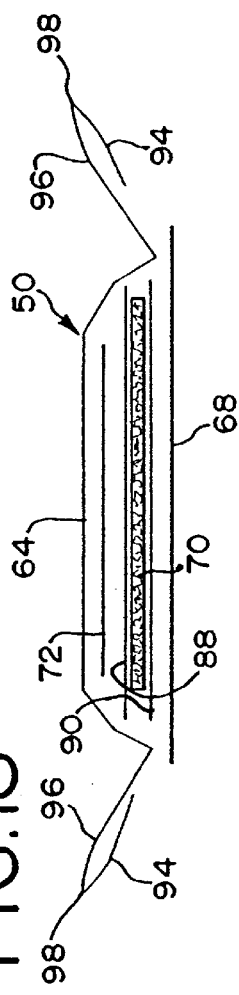
FIG. 18 is a schematic illustration of a cross-sectional view of the absorbent garment taken along line 18-18 in FIG. 17.
Figure 19:
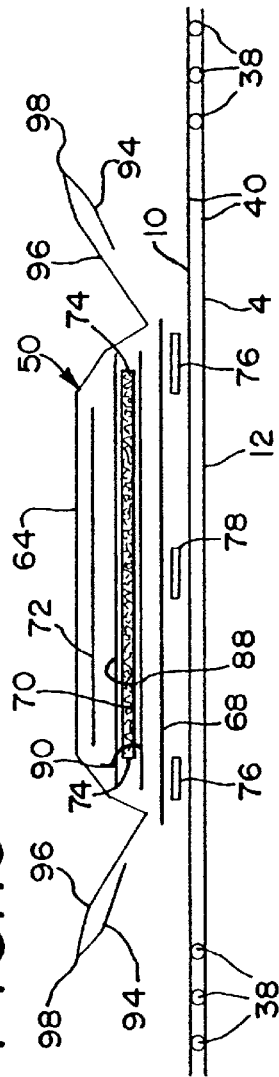
FIG. 19 is a schematic illustration of a cross-sectional view of the absorbent garment taken along line 19-19 in FIG. 17.
Figure 20:
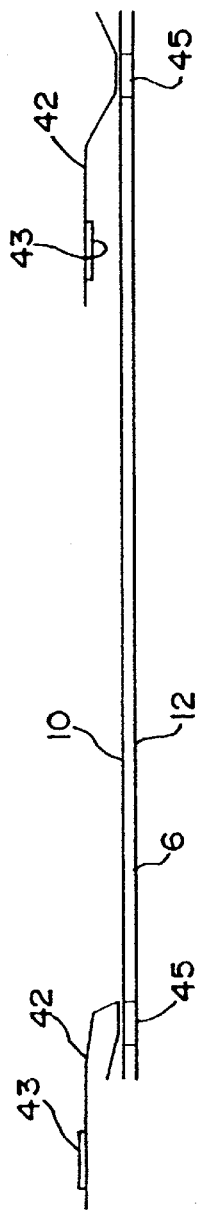
FIG. 20 is a schematic illustration of a cross-sectional view of the absorbent garment taken along line 20-20 in FIG. 17.

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user. The terms "upper," "lower," "inner", and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "bodyside," which means the side closest to the body of the user, while the terms "outer" and "lower" refer to a "garment side". The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

Referring to FIGS. 1, 3, 4, 5, 9, 13, 17, 20 and 21, an absorbent garment 2 includes a first, front body panel 4 and a second, rear body panel 6. The first and second body panels each have an inner, bodyside surface 10 an outer, garment side 12 surface and a length, which is less the overall length of the absorbent garment. Each of the first and second body panels has a first and second longitudinally opposed terminal end edges 16, 14, 20, 18, and outer side edges, including a tapered edge 22, 26 and an outboard edge 24, 28 formed along the outer periphery of laterally opposed ear portions 30, 32. Alternatively, as shown in FIGS. 29 and 30, the front body panel does not include a tapered side edge, but rather the terminal end edge extends The first terminal edges 14, 16 of the first and second body panels are longitudinally spaced to form an opening 34 therebetween in the crotch region of the garment, while the second terminal edges 20, 18 of the first and second body panels form front and back waist edges respectively. A plurality, meaning two or more, of laterally extending elastic elements 36 can be secured to each of the first and second body panels. Likewise, one or more leg elastic elements 38 can be secured along the tapered side edge of the body panels to form a gasket with the leg of the user. For example, as shown in FIGS. 1–4, each panel can be made of an elasticized composite panel material comprising two non-woven substrates 40 with the plurality of elastic strands 38, 36 sandwiched therebetween. The elastic strands are positioned in the waist regions and along the leg perimeters. A portion of the leg elastic elements 38 can extend under a side margin of an absorbent composite 50. The placement of the panel leg elastic elements further inward along the side edge provides for improved fit and performance of the garment.

For example, as shown in FIGS. 1-4, each panel can be made of an elasticized composite panel material comprising two non-woven substrates 40 with the plurality of elastic strands 38, 36 sandwiched therebetween. The elastic strands are positioned in the waist regions and along the leg perimeters. A portion of the leg elastic elements 38 can extend under a side margin of an absorbent composite 50. The placement of the panel leg elastic elements further inward along the side edge provides for improved fit and performance of the garment.

Figure 21:
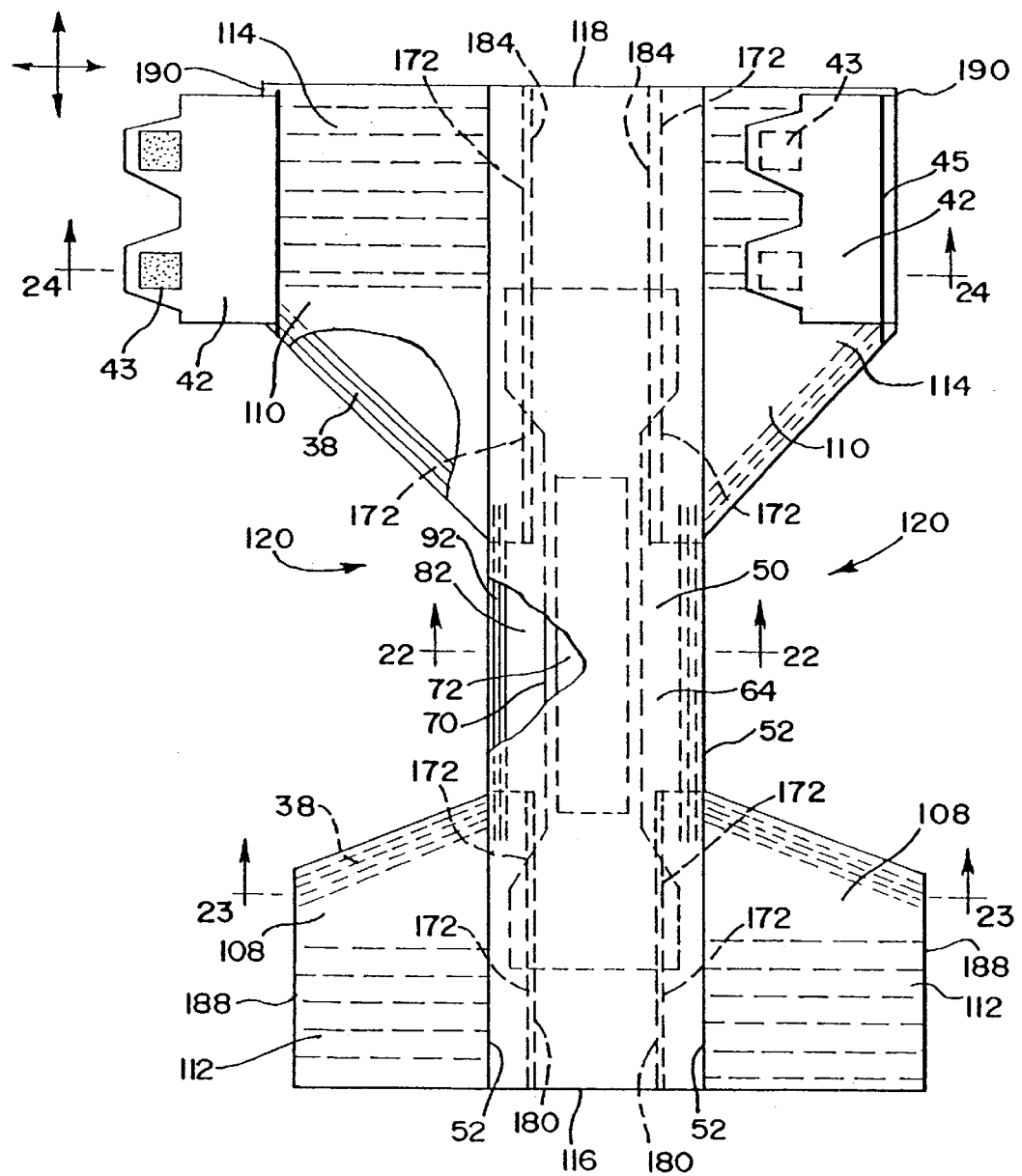
FIG. 21 is a plan view of a sixth embodiment of an absorbent garment taken from the bodyside thereof with a portion of the garment partially cut away.
Figure 25:
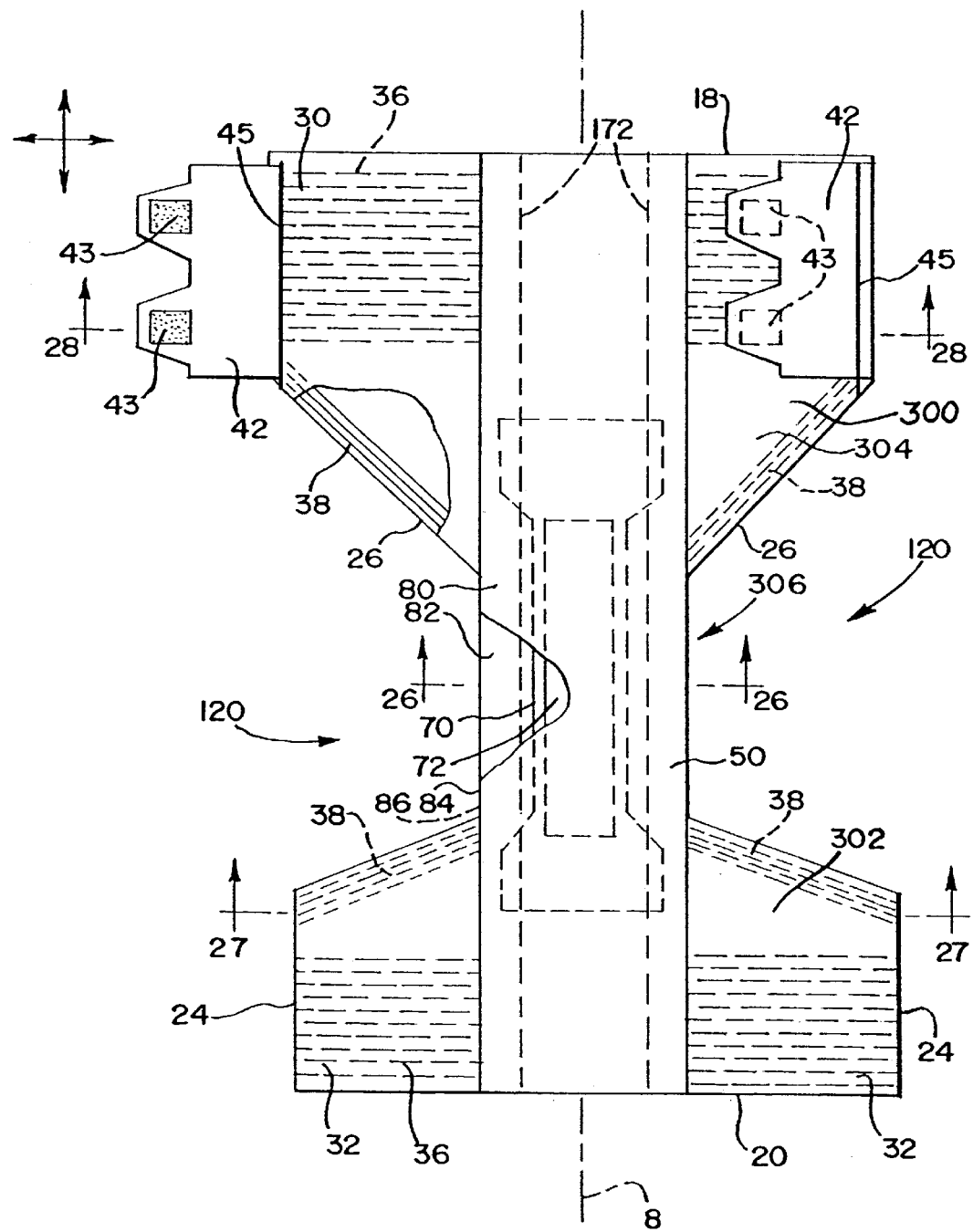
FIG. 25 is a plan view of a seventh embodiment of an absorbent garment taken from the bodyside thereof with a portion of the garment partially cut away.

In an alternative embodiment, shown in FIG. 21, an absorbent composite 50 extends longitudinally along the entire extent of the garment from one end 116 to the other end 118 thereof. A pair of front, side body panels 108 have inboard edges 180 that are secured to opposite side regions of the absorbent composite, preferably on the bodyside thereof, adjacent one end thereof and inboard from a peripheral side edge 52 of the absorbent composite. Likewise, a pair of rear, side body panels 110 have inboard edges 184 that are secured to opposite side regions of the absorbent composite, preferably on the bodyside thereof, adjacent the opposite end thereof and inboard from the peripheral side edge 52. The body panels 108, 110 extend laterally outward from the absorbent composite and form ear portions 112, 114 having outboard edges 188, 190. It should be understood that the absorbent composite could alternatively be secured to the garment side of the body panels.

Referring to FIGS. 1, 5, 9, 13, 17 and 21, fastening tabs 42 are attached and extend laterally from the outboard edge 28, 190 of the rear body panels from an attachment location 45. It should be understood that the fastening tabs could be affixed to the front body panels or to both the front and rear body panels. For the purposes of illustration, the right side tab 42 is shown as being folded in during manufacture, while the left side tab 42 is shown as being extended outboard during use. The fastening tabs can be made of a hook and loop combination, such as a Velcro®fastening system, or can have adhesive or other bonding agents applied to one surface thereof. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of suitable hook fasteners are the various CS600 hook fasteners manufactured by Minnesota Mining and Manufacturing Co., St. Paul Minn.

As shown in FIG. 1, the tab 42 can include one or more attachment pads 43. Alternatively, the fastening tabs can include buttons, snaps, ties or other known fastening devices. The tabs can be secured to the body panel with adhesive bonds, sonic bonds, thermal bonds, pinning, stitching or other known types of attachment.

When the absorbent garment is secured to the user, the fastening tabs 42 secured to the body panels 6, 110 on one end of the absorbent composite engage or are otherwise connected to the body panels 4, 108 on the opposite end of the garment. Alternatively, a landing member, which is particularly suited for engaging the fastening tabs and in particular the attachment pads, can be disposed on the body panel. For example, a pattern-unbonded material, as disclosed for example in U.S. Pat. No. 5,858,515 to Stokes, which is hereby incorporated by reference, is particularly well-suited for engaging a hook material. Other landing materials can be incorporated that are suitable for engaging adhesives and the like. When secured in this way, openings 120 are formed on each side of the absorbent composite with the peripheral edge 52, 152 of the absorbent composite further defining the opening along the crotch region of the garment. When secured, the front and rear body panels 108, 110 form opposite side body panels.

It should be understood that the outboard edges 24, 28, 188, 190 of the front and rear body panels could be connected, for example by bonding or sewing, to create a seam of a pant garment. For example, the embodiments of FIGS. 29 and 30 are shown without fastening tabs, wherein the outboard edges 24 and 28 are secured to form a seam. However, it should be understood that fastening tabs could be incorporated into those embodiments. Alternatively, the front and rear body panels can be formed integrally, for example as a single side panel attached to opposite ends 116, 118 of the absorbent composite, or as one panel extending around the waist and hips of the user. In yet another alternative embodiment, the outboard edges can be connected to create a seam in combination with fastening tabs, which can be used for example and without limitation to secure the body panels across a line of weakness, such as a perforation. The line of weakness can be formed for example along a breakable seam between the front and rear body panels, or along a length of one or both of the front and rear body panels.

In particular aspects of the invention, either or all of the body panels may be composed of a wide range of materials with various basis weights and properties. For example, the body panel material may include knitted or other woven fabrics, nonwoven fabrics, polymer films, laminates, and the like, as well as combinations thereof. Preferably, the body panels are made of an elastic material, wherein the term "elastic" means capable of recovering the size and shape thereof after deformation, and/or exhibiting a retractive force.

In the various configurations of the invention, the basis weight of the body panel material can be at least a minimum of about 10 g/m$^2$. Alternatively, the basis weight can be at least about 20 g/m$^2$, and optionally, can be at least about 40 g/m$^2$ to provide improved benefits. In further aspects, the basis weight of the body panel material can be not more than a maximum of about 100 g/m$^2$. Alternatively, the basis weight can be not more than about 80 g/m$^2$, and optionally, can be not more than about 60 g/m$^2$ to provide improved performance.

In the differing configurations of the invention, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material which is elastomerically stretchable at least along the lateral article width. Examples of such elastomeric materials can include a neck-bonded-laminate (NBL), a stretch-bonded-laminate (SBL), a necked-thermal laminate, or the like, as well as combinations thereof. Such laminates can provide an improved combination of cloth-like feel and elastomeric stretchability. The body panels can be composed of materials that are elastic or elastomeric and exhibit biaxial stretch characteristics or MD/CD stretch characteristics, or that are extensible composites.

In desired configurations, the elastomeric body panel material can provide an elastomeric, stretch elongation which is at least about 20%, and desirably is at least about 50%. Alternatively, the stretch elongation can be at least about 75%, and optionally, can be at least about 100% to provide improved performance. In other aspects, the elastomeric stretch elongation can be not more than about 400% and desirably can be not more than about 200%. Alternatively, the stretch elongation can be not more than about 300%, and optionally can be not more than about 250% to provide improved performance.

The percentage of elastomeric stretch or other elongation can be determined in accordance with the following formula:

$$100*(L-L_o)/L_o;$$

where:
L=stretched length,
L$_o$=initial length,

In addition, the amount of stretch elongation is determined under an applied tension force of 250 gram-force per inch of width measured perpendicular to the direction of the applied tension. Various configurations and materials of the body panels are further shown and described in U.S. Pat. No. 6,132,410 directed to a "Disposable Garment Having Dryness Barriers With Expandable Attachment To An Absorbent," the entire disclosure of which is hereby incorporated herein by reference.

The body panels also can be made of extensible materials, or combinations of elastomeric and extensible materials. It should be readily appreciated that each of the individual body panels may be composed of different materials, or of substantially the same material.

The term extensible means capable of being extended, and that it provides a selected elongation when subjected to an applied tensile force. The body panel also is preferably capable of providing a selected, sustained deformation when subjected to an applied tensile force and then allowed to relax for a selected time period beginning immediately after removal of the tensile force. Preferably the sustained deformation is substantially permanent deformation. The selected elongation and sustained deformation preferably occur at least along the lateral cross-direction of the garment, although it should be understood that it also could occur along the longitudinal direction, or both. Various extensible materials, and other acceptable materials that can be used for the body panels and the absorbent composite, which may include without limitations a retention portion, a topsheet and a backsheet, are described in U.S. application Ser. No. 09/249,434 filed Feb. 12, 1999, entitled Expandable Cover Garment, the entire disclosure of which is hereby incorporated herein by reference.

Referring again to FIGS. 1-4, the absorbent composite 50 has first and second longitudinally opposed end regions 56, 58 and first and second longitudinally opposed terminal end edges 60, 62. The absorbent composite includes a substantially liquid permeable topsheet 64, or liner, and a substantially liquid impermeable backsheet 68, or barrier layer. A retention portion 70 is disposed or sandwiched between the topsheet and the backsheet, which are connected, at least along their peripheral edges. The absorbent composite, and in particular the retention portion, can be made in many different shapes, including rectangular and hour-glass shapes.

The topsheet and backsheet can be minimally attached, e.g. at the peripheral edges, or they can be attached across substantially the entire surface area thereof. The topsheet and backsheet can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. Additional layers, including for example, a surge layer 72, can also be incorporated into the absorbent composite. Preferably, the surge layer does not run the entire length of the absorbent composite and is shorter than the retention portion. In alternative configurations, the topsheet is indirectly joined to the backsheet by affixing the topsheet to intermediate layers, such as the surge layer or retention portion, which in turn is affixed to the backsheet.

The topsheet 64 presents a body-facing surface that is compliant, soft-feeling, and non-irritating to the wearer's skin. Further, the topsheet 64 can be less hydrophilic than retention portion 20, and is sufficiently porous to be liquid permeable, permitting liquid to readily penetrate through its thickness to reach the retention portion. A suitable topsheet layer 64 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 64 is typically employed to help isolate the wearer's skin from liquids held in the retention portion.

Various woven and nonwoven fabrics can be used for topsheet 64. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise process to impart a desired level of wettability and hydrophilicity. In a particular embodiment of the invention, topsheet 64 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton®X-102 surfactant. The surfactant can be applied by any conventional means, such as spraying, printing, brush coating or the like.

In various embodiments, as described below, the topsheet can be made of extensible materials, as described with respect to the body panels and backsheet. For example, the topsheet can be prenecked for extensibility.

The backsheet 68 is preferably liquid impermeable, but may be liquid permeable, e.g., when a barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In other alternative constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a Huggies®Ultratrim Disposable Diaper, which has been commercially available from Kimberly-Clark Corporation. The backsheet 68 typically provides the outercover of the article. Optionally, however, the article may include a separate outercover component member which is additional to the backsheet. The outercover can be joined, for example, to one or more of the aborbent composite and/or body panels.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet is preferably extensible, as that term is defined above with respect to the body panels. In one preferred embodiment, the backsheet is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible backsheet can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 70 is preferably made of an absorbent material, which tends to swell or expand as it absorbs liquid excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material.

In one preferred embodiment, an absorbent material is made of fibrous absorbent materials with a relatively high internal integrity, including for example one made with thermoplastic binder fibers in airlaid absorbents, e.g., pulp, bicomponent binding fibers, and superabsorbents, which have higher densities in the folded regions. The higher density and resulting smaller capillary size in these regions promotes better wicking of the liquid. Better wicking, in turn, promotes higher utilization of the absorbent material and tends to result in more uniform swelling throughout the absorbent material as it absorbs the liquid.

Various types of wettable, hydrophilic fibrous material can be used to form the component parts of absorbent, and particularly the retention portion 70. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

In particular arrangements, the retention portion of the absorbent may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent composite and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent composite and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bods, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vingyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975, which is hereby incorporated herein by reference. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al., both of which are hereby incorporated herein by reference.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent is generally in the form of discrete particles. The particles can be of any desired shape, for example, spiral or semi-spiral, cubic, rod-like, polyhedral, etc. Shapes having a large greatest dimension/smallest dimension ration, like needles, flakes and fibers, are also contemplated for use herein. Conglomerates of particles of absorbent gelling material may also be used in the absorbent. Desired for use are particles having an average size of from about 20 microns to about 1 millimeter. "Particle size" as used herein means the hydrophilic fibers and high-absorbency particles can be configured to form an average composite basis weight which is within the range of about 50-1500 gsm. In certain aspects of the invention, the average composite basis weight is within the range of about 200-1200 gsm, and alternatively is within the range of about 200-1200 gsm, and alternatively is within the range of about 500-800 gsm to provide desired performance. Furthermore, the proportion of high absorbency particles can range from about 0 to about 100% and the proportion of fibrous material from about 0 to about 100%. Additionally, high absorbency fibers can be used such as Oasis Type 121 and Type 122 superabsorbent fibers available from Technical Absorbent Ltd., Grimsby, Lincolnshire, United Kingdom.

The retention portion 70 has laterally opposed side edges 74 and preferably is made of a single layer of material. As shown in FIG. 29, the absorbent composite 50 and retention portion 70 have a generally rectangular shape. Alternatively, as shown in FIGS. 1 and 30, the retention portion 70 has an hour-glass shape, with a narrower middle portion and enlarged end portions. The absorbent composite, and in particular the top sheet and backsheet also can be configured in an hour-glass shape with enlarged end regions. In other alternative embodiments, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper and lower tissue substrate 88, 90 also can be disposed adjacent the retention portion, or alternatively the tissue can completely envelope the retention position.

Referring to FIG. 1, the opposite garment side of the end regions 56, 58 of the absorbent composite, and in particular, the outer, garment side surface of the backsheet 68, are secured to the bodyside surface of the longitudinally opposed crotch ends of the first and second body panels 4, 6. Preferably, the garment side surface of the end regions 56, 58 overlap and are connected to the bodyside surface of the body panels along three longitudinally extending, parallel, spaced locations 76, 78. It should be understood that the absorbent composite can be secured using any of the methods of attachment described above, including for example and without limitation, adhesive bonds, sonic bonds, thermal bonds, pinning, stitching or other attachment techniques known in the art, as well as combinations thereof. Moreover, it should be understood that the three locations are meant to be illustrative, and that the lateral width (W) of the absorbent composite defined between the opposite outboard edges of attachment can be secured to the body panels with any configuration of attachment lines, swirls, patterns, spots, etc., or can be a full and continuous attachment therebetween. The outboard attachment locations 76, or the outboard edge of the area of attachment, are preferably spaced inboard from the side edge 52 of the absorbent composite, preferably slightly outboard of the side edges 74 of the retention portion. The retention portion 70 preferably has a lesser lateral width than the overall absorbent composite.

In particular, in the embodiment shown in FIGS. 1-4, the backsheet and topsheet have laterally extending side margins 82, 80 that extend laterally outboard from the side edge 74 of the retention portion and from the location 76 of attachment to the body panels. It should be understood that the term "location" means any region, dot, position or side, and is not limited to the longitudinally extending lines shown in the Figures. For example, the location could comprise a series of longitudinally extending dots or points. Conversely, the location could comprise a continuous region or area attachment extending across the lateral width (W) of the absorbent composite between the outboard edges of the attached region of the absorbent composite. The term "attached region" means the region extending between the opposite outboard edge of the attachment locations, and is shown, for example, as having a width W in FIG. 3. The side margins 80, 82 are preferably formed along the entire longitudinal extent of the portion of the absorbent composite that overlaps the body panels, and also extend along the crotch and the absorbent composite between the body panels. The side margins 80, 82 are not attached to the body panels 4, 6 and terminate in free edges 84, 86.

It should be understood that the side margins may extend along only a portion of the overlapping absorbent composite. For example, and referring to FIGS. 29 and 30, the absorbent composite 50 is connected to each of the body panels 4, 6 with a T-shaped attachment pattern 176, 178, or location. In particular, the garment side surface of the end regions 56, 58 of the absorbent composite overlap and are connected to the body side surface of the body panels 4, 6 along a longitudinally extending location 180, 184 at a center portion of the absorbent composite and of the body panels, and also along laterally extending locations 182, 186 at each end of the absorbent composite, thereby forming the stepped, T-shaped pattern. Preferably, the laterally extending attachment locations 182, 186 at the four corners at the ends of the absorbent composite, in combination with the portion of the longitudinally extending location at the end of the absorbent composite, forms a laterally extending attachment location that extends along substantially the entirety of the width of the absorbent composite at the end thereof. In an alternative embodiment, the absorbent composite 50 is secured to the body panels only at the four corner locations 182, 186, with the space therebetween remaining unattached to the body panels. The length of the laterally extending attachment locations can vary from almost nothing, wherein just the end or edge of the absorbent composite is secured to the body panel at those locations 182, 186, to almost the entirety of the length of the absorbent composite that overlaps the body panel. Indeed, in one alternative embodiment, the entirety of the absorbent composite that overlaps the body panel can be secured thereto.

A side margin 188, 190 extends laterally outward from each side of the longitudinal location 180, 184 at the center portion and terminates in a free edge 192, 194. In addition, the side margins 188, 190, and the free edges 192, 194, extend longitudinally inward along the length of the absorbent composite from the lateral attachment locations 182, 186 at the ends of the absorbent composite. In this way, the four corners 182, 186 of the absorbent composite are secured to the body panels, yet the absorbent composite is provided with opposite side margins extending along the length of the portion of the absorbent composite overlapping the body panels inward from those locations on each side of the absorbent composite. In this way, the side margins are prevented from being folded over the absorbent area of the absorbent composite so as to impede the absorption of exudates. It should be understood that the side margins 188, 190 shown in FIGS. 29 and 30 can be formed from any of the topsheet, backsheet, or combination thereof, or any other component of the absorbent composite, with or without folds, as variously disclosed herein.

In a preferred embodiment, the width of the portion of the side margin overlapping the body panels between the longitudinal location and the free edge remains relatively constant. It should be understood that in other embodiments, the width can vary, as shown for example in FIG. 17 as explained below, or as that width is defined between other non-parallel and/or curvilinear configurations of the attachment locations and free edges.

It should be understood that in an alternative embodiment, the retention portion, or one or more other layers including for example the surge layer or tissue layers, also can have opposite side margins that extend outboard from the locations 76 of attachment to the body panels and are sandwiched between the side margins 80, 82.

The side margins preferably have a lateral width greater than about 3 mm and less than about 75 mm. More preferably, the side margins each have a width of between about 15 mm and about 45 mm, and more preferably a width of between about 25 mm and about 35 mm. Preferably, the side margins have a combined lateral width that is at least 3% and not more than about 75% of the total lateral width of the absorbent composite, and more preferably between about 15% and 50% of the total lateral width, and even more preferably between about 25% and 35%. The body panels extend beyond the lateral and longitudinal edges of the side margins of the absorbent composite.

In the embodiments shown in FIGS. 5–8, 29 and 30, one or more elastic elements 92, shown as three, are secured in the side margins 80, 82 between the topsheet and backsheet, and extend longitudinally along a portion of the side margins on each side of the absorbent composite. Preferably, the elastic elements extend along the side margins of the absorbent composite between the body panels and overlap a portion of each body panel 4, 6. The length of the elastic elements is preferably between about 5% and 100% of the length of the absorbent composite. For example, as shown in FIG. 29, the elastic elements extend along the side margins from the lateral attachment location at the end of the absorbent composite secured to the front body panel across the terminal edge of the rear body panel. The function of the elastic elements in the side margins of the absorbent composite are to shorten the length of the side margin which pulls the side margins inwardly to form a three-dimensional profile so as to seal or gasket against the body of the user. At the same time, in the embodiments of FIGS. 17, 29 and 30, the attachment of the absorbent composite at the four corners prevents the side margins from being folded or drawn over the absorbent area. In addition, assembly of the garment is facilitated since the absorbent composite lies flat when the elastic elements are stretched in the machine direction. The elastic elements can be positioned at various laterally spaced positions, depending on the amount of shortening and upward lift desired. The elastic elements can be made of ribbon, films, sprays of elastic, or other elastic configurations know in the art. It should be understood that elastic elements can be incorporated into any of the other side margin configurations described herein.

In a third embodiment shown in FIGS. 9-12, the topsheet side margin 80 includes a first portion 94 folded over a second portion 96, with a side margin portion 82 of the backsheet disposed between the first and second portions 94, 96 of the topsheet. The folded first and second portions 94, 96 form a folded edge 98 that defines the free edge of the side margin of the absorbent composite. The function of the folded topsheet is to provide a clothlike feel to the portion 82 of the backsheet that forms the side margin. Preferably, the topsheet covers at least the free edge 86 of the backsheet, which provides comfort to the user with minimal cost.

In yet another embodiment shown in FIGS. 25-28, the body panel 300 is continuous from the rear of the garment through the crotch region to the front of the garment. In such an embodiment, the absorbent composite can be attached to the front 302, rear 304 and crotch 306 portions of the body panel. In essence, a crotch body panel extends between and connects a front and rear body panel. The body panel 300 is preferably made of continuous sheets or layers that form the three regions, although it should be understood that separate pieces can be joined, e.g., by bonding, stitching etc., to form the full length body panel.

In one embodiment, the two locations 172 of attachment would extend the length of the absorbent composite. In one embodiment, shown in FIG. 26, the body panel width in the crotch region 306, defined by outboard edges 310, extends between the outboard attachment locations, or is preferably substantially the same width as the width "W" of the attached region, and more preferably is substantially the same width as the retention portion. In an alternative embodiment, the body panel extends outboard from the attachment locations, but remains unattached to the side margins of the absorbent composite. Preferably, the absorbent composite extends substantially the entire length of the garment, although it should be understood that it could have a length less than the entire length of the garment, as shown for example in FIG. 1.

In another embodiment, shown in FIGS. 13-16, the side margin is formed only by the topsheet, with the backsheet having side edges terminating proximate the attachment locations. Preferably, the topsheet has a folded first and second portion 94, 96 forming a folded edge 98 that defines the free edge of the side margin. Conversely, it should be understood that the side margin can be formed only by the backsheet, which can be monolayer, or which can have various folds, including for example a folded first and second portion. It should be understood that the first portion can be folded under the second portion, as shown in the Figures, or folded over the second portion. It also should be understood that the side margin could have additional folds, formed for example by a third portion interfolded with the first and second portions. Preferably, each side margin or the side margins in combination have a width or range of widths as described above.

In another embodiment, shown in FIGS. 17-20, the side margin 80 is tapered from a first width D1 adjacent a first position 102 at the terminal edge of the body panel to a second width D2 adjacent a second position 104 at the end of the end edge of the absorbent composite. In one embodiment, the second width is zero. Preferably, D1 ranges from not less than about 5% to not greater than about 50% of the total lateral width of the absorbent composite. Preferably, D2 ranges from about 0 to not greater than about 50% of the total lateral width of the absorbent composite. The gradient attachment location 106 allows the marginal side edges of the absorbent composite to fold inwardly in the crotch region during use to gasket with the user, while the attachment at the end regions provides and maintains the area of coverage of the absorbent composite in the front and back panels without affecting the fit of the garment. In particular, as with the embodiments of FIGS. 29 and 30, the four corners of the absorbent composite 50 are secured to the body panels to prevent the side margins 80 from folding over the absorbent area, yet the absorbent composite is provided with opposite side margins extending along the length thereof between those locations on each side of the absorbent composite.

In another embodiment, shown in FIGS. 21-24, the absorbent composite 50 extends substantially the entire length of and defines the length of the absorbent composite and preferably the absorbent garment. Each of the bodyside surfaces of the inboard terminal edges 180, 184 of the front and back side panels 108, 110 are secured to the absorbent composite along a location 172 spaced laterally inboard from the side edge 52 of the absorbent composite so as to form opposite side margins 80, 82. As such, the side margins extend the entire longitudinal length of the body panels and the garment. It should be understood that although the side margins 80, 82 are shown as being formed from the backsheet and topsheet, without a folded edge, any of the above-described side margin configurations could be used, including a folded topsheet configuration. Indeed, it should be understood that any of the aforementioned configurations of the side margins, whether formed from one or both of the backsheet and topsheet, with or without folded portions and with or without elastic elements, can be incorporated into an absorbent composite attached to any of the aforementioned body panel configurations, or their equivalents, including without limitation, a continuous one-piece body panel (whether made from one or more layers or plies), a two-piece body panel, or a four piece body panel.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An absorbent garment comprising:
    longitudinally spaced first and second body panels each having a bodyside surface, a terminal waist edge and a terminal crotch edge, wherein said crotch edges of said first and second body panels are longitudinally spaced apart and define a gap therebetween and wherein said waist edges of said first and second body panels are longitudinally spaced apart; and
    an absorbent composite having a longitudinally extending length, a laterally extending width and longitudinally opposed first and second end regions having respective first and second ends, said absorbent composite comprising a backsheet, a topsheet and a retention portion disposed between said backsheet and said topsheet, wherein said absorbent composite bridges said gap between said crotch edges of said first and second body panels and wherein said first end region of said absorbent composite overlaps and is connected to said bodyside surface of said first body panel along a longitudinally extending center portion thereof and across an entirety of said width of said absorbent composite at said first end thereof, and wherein said second end region of said absorbent composite overlaps and is connected to said bodyside surface of said second body panel along a longitudinally extending center portion thereof and across an entirety of said width of said absorbent composite at said second end thereof, wherein said absorbent composite comprises a pair of laterally opposed side margins terminating in opposite, longitudinally extending outboard free edges, respectively, wherein said side margins are not attached to said first and second body panels and wherein each said longitudinally extending free edge extends between the connection across said width of said absorbent composite at said first end thereof to the connection across said width of the absorbent composite at said second end thereof, and wherein first and second portions of each of said side margins overlapping said first and second body panels respectively between said center portion and said free edge each have a relatively constant width between said center portion and said free edge.

2. The absorbent garment of claim 1 wherein said side margins are formed from said backsheet.

3. The absorbent garment of claim 1 wherein said side margins are formed from said topsheet.

4. The absorbent garment of claim 3 wherein said side margins each comprise a first portion of said topsheet folded over a second portion of said topsheet, wherein said folded first and second portions form a folded edge defining said free edge of each of said side margins.

5. The absorbent garment of claim 4 wherein said side margins further comprise a portion of said backsheet disposed between said first and second portions of said topsheet.

6. The absorbent garment of claim 1 wherein said side margins are formed from said topsheet and said backsheet.

7. The absorbent garment of claim 1 wherein said side margins each comprise a longitudinally extending elastic element.

8. The absorbent garment of claim 7 wherein each of said elastic elements extends along only a portion of said length of said absorbent composite.

9. The absorbent garment of claim 1 wherein said first and second end regions of said absorbent composite are each connected to said first and second body panels respectively with a T-shaped attachment pattern, wherein said connection between each of said first and second end regions and said first and second body panels respectively along said center portion and across said width of each of said first and second ends of said absorbent composite define said T-shaped attachment patterns.

10. The absorbent garment of claim 1, wherein the portions of said first and second body panels overlapped respectively by said first and second end regions of said absorbent composite are not elasticized.

11. The absorbent garment of claim 1 wherein the connection along each of said center portions is formed as a continuous line of attachment.

* * * * *